United States Patent
Chen et al.

(10) Patent No.: US 7,381,717 B2
(45) Date of Patent: *Jun. 3, 2008

(54) ANTI-HIV AGENTS WITH DUAL SITES OF ACTION

(75) Inventors: Chin Ho Chen, Chapel Hill, NC (US); Li Huang, Chapel Hill, NC (US)

(73) Assignee: Meharry Medical College, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/348,052

(22) Filed: Feb. 6, 2006

(65) Prior Publication Data

US 2006/0135495 A1 Jun. 22, 2006

Related U.S. Application Data

(63) Continuation of application No. 10/413,193, filed on Apr. 14, 2003, now Pat. No. 7,026,305.

(51) Int. Cl.
*A61K 31/56* (2006.01)
*C07J 53/00* (2006.01)

(52) U.S. Cl. ..................... 514/169; 552/510

(58) Field of Classification Search ............. 552/510; 514/169
See application file for complete search history.

(56) References Cited

U.S. PATENT DOCUMENTS

| | | |
|---|---|---|
| 5,468,888 A | 11/1995 | Bouboutou et al. |
| 5,679,828 A | 10/1997 | Lee et al. |
| 5,962,527 A | 10/1999 | Pezzuto et al. |
| 6,048,847 A | 4/2000 | Ramadoss et al. |
| 6,172,110 B1 | 1/2001 | Lee et al. |
| 6,369,101 B1 | 4/2002 | Carlson |
| 6,369,109 B1 | 4/2002 | Debatin et al. |
| 6,403,816 B1 | 6/2002 | Jaggi et al. |
| 6,458,834 B2 | 10/2002 | Glinski et al. |
| 6,495,600 B1 | 12/2002 | Pezzuto et al. |

OTHER PUBLICATIONS

Ma et al. "Chemical Modification of Oleanene Type Triterpenes and their Inhibitory Activity Against HIV-1 Protease Dimerization" *Chem Pharm Bull* 48(11): 1681-1688 (2000).

*Primary Examiner*—Barbara P. Badio
(74) *Attorney, Agent, or Firm*—Myers Bigel Sibley & Sajovec, P.A.

(57) ABSTRACT

The present invention provides compounds of the general structure:

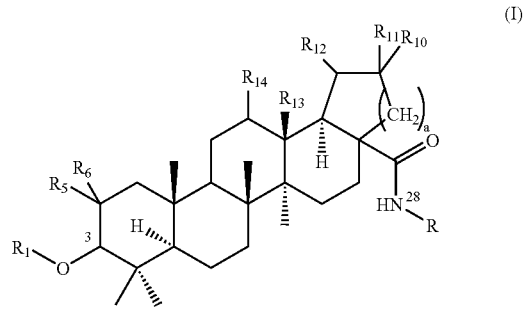

which are substituted at the 3 and 28 positions, along with pharmaceutical formulations containing the same and methods of treating viral infections employing the same.

15 Claims, 3 Drawing Sheets

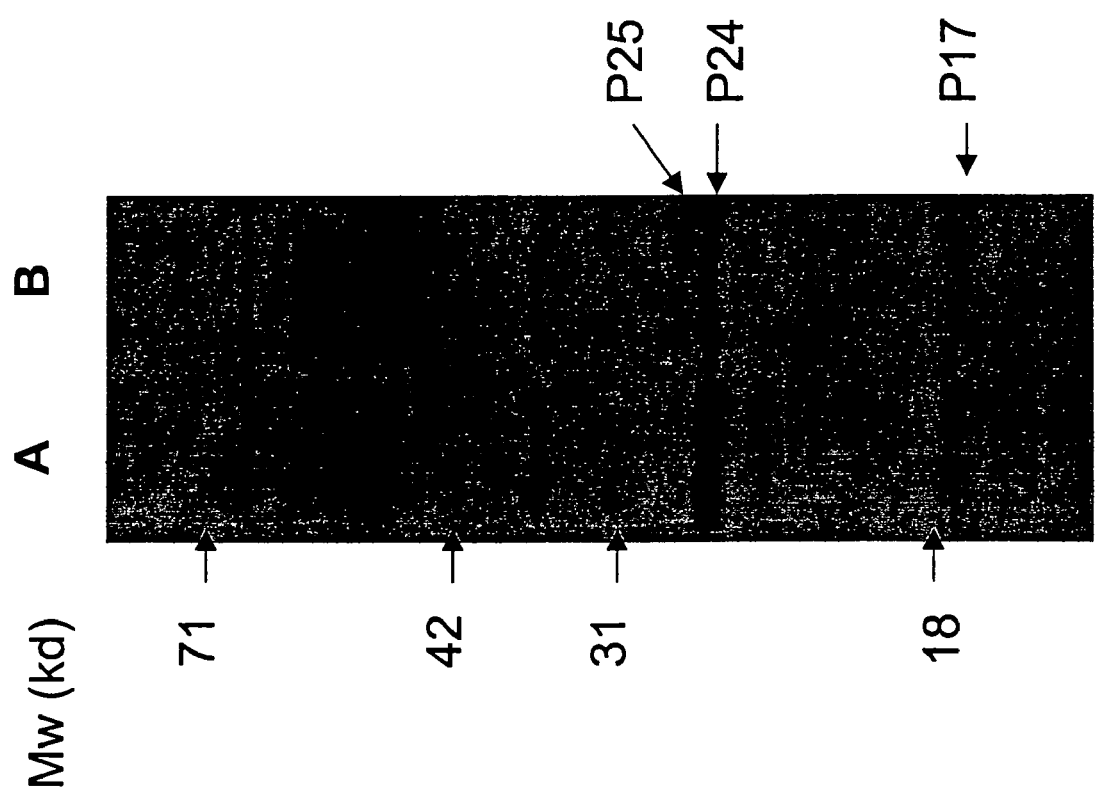

ANTI-HIV AGENTS WITH DUAL SITES OF ACTION

RELATED APPLICATIONS

This application claims priority to and is a continuation of patent application Ser. No. 10/413,193, filed Apr. 14, 2003 now U.S. Pat. No. 7,026,305, the disclosure of which is hereby incorporated herein by reference.

FIELD OF THE INVENTION

The present invention concerns compounds, compositions and methods useful for the treatment of retroviral infections in human or animal subjects in need thereof.

BACKGROUND OF THE INVENTION

Retroviruses are small, single stranded RNA viruses. Numerous species are susceptible to retroviral infection. While retroviral infection does not necessarily interfere with the normal life cycle of an infected cell or organism, retroviruses can be oncogenic, and retroviruses are responsible for diseases of the immune system in higher animals, including acquired immune deficiency syndrome (AIDS), caused by the human immunodeficiency virus (HIV).

Progress has been made in the development of drugs for HIV therapy. Among other things, U.S. Pat. No. 6,172,110 to Lee et al. describes acylated betulins for the treatment of HIV, U.S. Pat. No. 5,679,828 to Lee et al. describes betulinic acid derivatives for the treatment of HIV, and U.S. Pat. No. 5,468,888 to Bouboutou et al. describes lupane derivatives for the treatment of HIV. Specific examples of compounds that have been described for the treatment of HIV are the following:

Nevertheless, many drugs exhibit severe toxicities, have side effects, require complicated dosing schedules, or—most problematically—can lead to the development of drug resistance thereto in the subject being treated. These problems are further exacerbated in countries where high cost multiple drug therapy is not readily affordable to the general population. Hence there remains a need for new compounds useful for treating HIV, including for the treatment of strains of HIV that are resistant to treatment with other known compounds. There particularly remains a need for new compounds that have multiple modes of activity in treating HIV-1 infection.

SUMMARY OF THE INVENTION

A first aspect of the present invention is, accordingly, compounds useful for the treatment of a retroviral infection in need thereof.

A first aspect of the present invention is a compound according to Formula I:

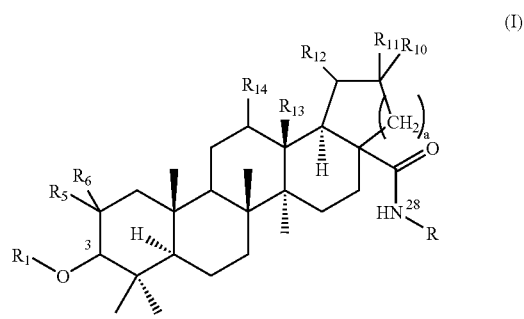

(I)

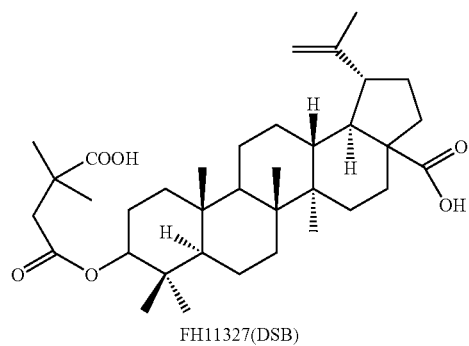

FH11327(DSB)

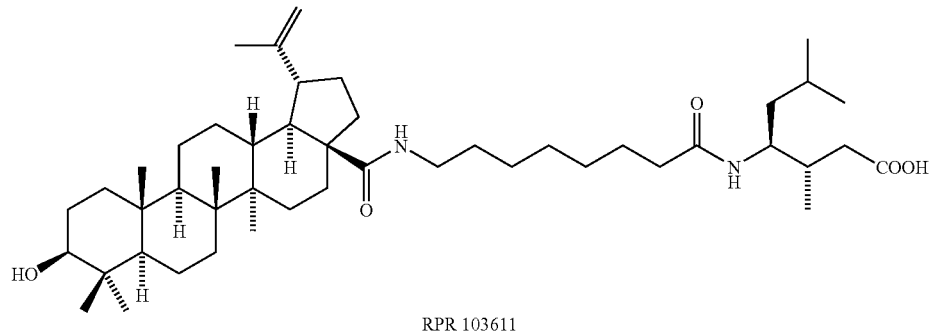

RPR 103611 wherein:

a is 1 or 2;

$R_{10}$ and $R_{11}$ are each either H or loweralkyl (e.g., methyl);

$R_{12}$ is H, loweralkyl (e.g., methyl), or $-CR_2R_3R_4$;

$R_{13}$ and $R_{14}$ are each either H or form a bond with one another (thus forming a double bond between their immediately adjacent carbon atoms);

R is a substituent of the formula:

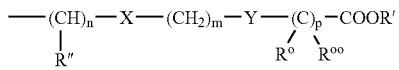

wherein:

R' and R" are the same or different, are hydrogen atoms or alkyl radicals,

X is a bond or represents a carbamoyl, N-methylcarbamoyl, aminocarbonyl or N-methylaminocarbonyl radical, Y is a bond or represents a phenylene radical, $R^o$ and $R^{oo}$ are the same or different, and are hydrogen atoms or alkyl radicals (it being understood that $R^o$ and $R^{oo}$ are not necessarily identical on each unit $-CR^oR^{oo}-$), or $R^o$ is hydroxyl, hydroxyalkyl, phenyl, benzyl, carbamoylmethyl or else, when Y is a bond and X is carbamoyl, $R^o$ can form a 5- or 6-membered ring with the nitrogen atom contained in X, it being possible for this ring to additionally comprise another hetero atom chosen from oxygen or sulphur and, n, m and p are each integers from 0 to 16, and m+n+p is between 4 and 16; or R is a substituent of the formula

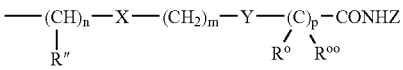

where R", $R^o$, $R^{oo}$, X, Y, n, m and p are as given above and Z is an amino acid radical such as a standard amino acid radical joined to the adjacent carbon atom illustrated by a peptide bond to the amino terminus of the amino acid (the group "NH" in the formula above thus being the amino terminus of the amino acid);

$R_1$ is a $C_2$ to $C_{20}$ substituted or unsubstituted carboxyacyl; or $R_1$ is a substituent of the formula

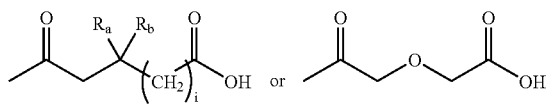

where $R_a$ and $R_b$ are the same or different and are each either hydrogen or loweralkyl, and i is an integer of from 0 to 3;

$R_2$ is a methyl radical or forms with $R_4$ a methylene radical or an oxo radical, $R_3$ is a hydroxyl, methyl or hydroxymethyl radical or a radical $-CH_2OR'_2$, $-CH_2SR'_2$ or $-CH_2NHR'_2$ for which $R'_2$ is alkyl, hydroxyalkyl, dihydroxyalkyl, acetamidoalkyl or acetyl, or $R_2$ is an amino radical substituted with a hydroxyalkyl or carboxyhydroxyalkyl radical, or a dialkylamino radical, the alkyl parts of which can form, with the nitrogen atom to which they are joined, a 5- or 6-membered heterocycle optionally containing another hetero atom chosen from oxygen, sulphur or nitrogen and, optionally, N-alkyl, $R_4$ is a hydrogen atom or forms, with $R_2$ or $R_3$, a methylene radical or an oxo radical, $R_5$ and $R_6$ are each hydrogen or together form an oxo radical;

or a pharmaceutically acceptable salt thereof.

A further aspect of the present invention is a composition comprising a compound of Formula I (an active compound) in a pharmaceutically acceptable carrier (such as an aqueous carrier).

A further aspect of the present invention is directed to methods for inhibiting a viral, particularly a retroviral infection (e.g., HIV-1 infection) in cells or tissue of an animal, or in an animal subject, comprising administering an effective retroviral inhibiting amount of a compound of Formula I. A preferred embodiment is directed to a method for treating a patient suffering from a retroviral-related pathology, comprising administering to said subject a retroviral inhibiting effective amount of a pharmaceutical composition that includes a compound of Formula I.

A fourth aspect of the present invention is the use of compounds as described above for the preparation of a medicament for carrying out a method as described above.

BRIEF DESCRIPTION OF THE DRAWINGS

FIG. 4. LH55-1 (compound 12) inhibits HIV-1 maturation. HIV-1 viral particles produced from ACH-2 cells in the absence (A) or presence (B) of LH55-1. The collected viral samples were lysed and analyzed by using a Western blot. The primary antibody used for the Western blot is a HIV-1 positive human serum. Mw: Molecular weight standards.

DETAILED DESCRIPTION OF THE PREFERRED EMBODIMENTS

Figure 1:
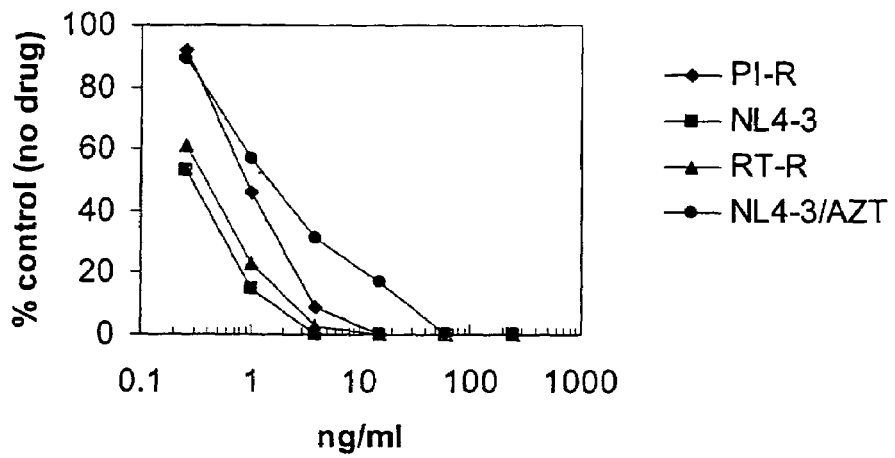
FIG. 1: Anti-HIV activity of N-[3-β-O-(3',3'-dimethylsuccinyl)-lup-20(29)-en-28-oyl]-11-aminoundecanoic acid (LH 55-1). PI-R: A multiple HIV-1 protease inhibitor resistant strain. RT-R: A multiple HIV-1 reverse transcriptase inhibitor resistant strain. NL4-3: A T-cell line adapted HIV-1 strain. NL4-3/AZT: The effect of the $1^{st}$ anti-HIV drug AZT on the NL4-3 virus.

"Acyl" as used herein means mean a $-C(O)R$ radical, where R is a suitable substituent.

"alkyl," as used herein, refers to a straight or branched chain hydrocarbon, preferably containing from 1 to 4, 6 or 10 carbon atoms (with loweralkyl referring to C1 to C4 alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like.

"Carboxy" as used herein means the radical $-C(O)OH$.

"Amino acid" as used herein has its conventional meaning in the art and includes, but is not limited to, amino acids with nonpolar R groups such as alanine, valine, leucine isoleucine, proline, phenylalanine, tryptophan, and methionine, amino acids with uncharged polar R groups such as glycine, serine, threonine, cysteine, tyrosine, asparagine, and glutamine, acidic amino acids (negatively charged at pH 6.0) such as aspartic acid and glutamic acid, basic amino acids (positively charged at pH 6.0) such as lysine, arginine, and histidine, as well as nonstandard amino acids such as ornithine, 2-napthylalanine, norvaline, norleucine, thienylalanine, 4-chlorophenylalanine, 3-benzothienyalanine, 4,4'-biphenylalanine, tetrahydro-isoquinoline-3-carboxylic acid, aminoisobutyric acid, alpha-aminonormalbutyric acid, 2,2-diphenylalanine, 4-thiazolylalanine, etc. Amino acids may be standard or naturally occurring amino acids, and may be alpha amino acids.

"Treat" as used herein refers to any type of treatment that imparts a benefit to a patient afflicted with a disease, including improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

1. Active Compounds.

The methods of the present invention include the administration of active compounds as described herein (e.g., compounds of Formula I), while pharmaceutical compositions of the present invention comprise active compounds in a pharmaceutically acceptable carrier or diluent.

Active compounds of the present invention include compounds of Formula I as follows:

(I)

wherein:

a is 1 or 2;

$R_{10}$ and $R_{11}$ are each either H or loweralkyl (e.g., methyl);

$R_{12}$ is H, loweralkyl (e.g., methyl), or —$CR_2R_3R_4$;

$R_{13}$ and $R_{14}$ are each either H or form a bond with one another (thus forming a double bond between their immediately adjacent carbon atoms);

R is a substituent of the formula:

$$—(CH)_n—X—(CH_2)_m—Y—(C)_p—COOR'$$
with $R''$ below $(CH)_n$ and $R^o$ $R^{oo}$ below $(C)_p$ wherein:

R' and R" are the same or different, are hydrogen atoms or alkyl radicals,

X is a bond or represents a carbamoyl, N-methylcarbamoyl, aminocarbonyl or N-methylaminocarbonyl radical, Y is a bond or represents a phenylene radical, $R^o$ and $R^{oo}$ are the same or different, and are hydrogen atoms or alkyl radicals (it being understood that $R^o$ and $R^{oo}$ are not necessarily identical on each unit —$CR^oR^{oo}$—), or $R^o$ is hydroxyl, hydroxyalkyl, phenyl, benzyl, carbamoylmethyl or else, when Y is a bond and X is carbamoyl, $R^o$ can form a 5- or 6-membered ring with the nitrogen atom contained in X, it being possible for this ring to additionally comprise another hetero atom chosen from oxygen or sulphur and, n, m and p are each integers from 0 to 16, and m+n+p is between 4 and 16; or R is a substituent of the formula $$—(CH)_n—X—(CH_2)_m—Y—(C)_p—CONHZ$$
with $R''$ below $(CH)_n$ and $R^o$ $R^{oo}$ below $(C)_p$ where R", $R^o$, $R^o$, X, Y, n, m and p are as given above and Z is an amino acid radical such as a standard amino acid radical joined to the adjacent carbon atom by a peptide bond to the amino terminus of the amino acid radical;

$R_1$ is a $C_2$ to $C_{20}$ substituted or unsubstituted carboxyacyl; or $R_1$ is a substituent of the formula:

where $R_a$ and $R_b$ are the same or different and are each either hydrogen or loweralkyl, and i is an integer of from 0 to 3;

$R_2$ is a methyl radical or forms with $R_4$ a methylene radical or an oxo radical, $R_3$ is a hydroxyl, methyl or hydroxymethyl radical or a radical —$CH_2OR_{12}$, —$CH_2SR'_2$ or —$CH_2NHR'_2$ for which $R'_2$ is alkyl, hydroxyalkyl, dihydroxyalkyl, acetamidoalkyl or acetyl, or $R_2$ is an amino radical substituted with a hydroxyalkyl or carboxyhydroxyalkyl radical, or a dialkylamino radical, the alkyl parts of which can form, with the nitrogen atom to which they are joined, a 5- or 6-membered heterocycle optionally containing another hetero atom chosen from oxygen, sulphur or nitrogen and, optionally, N-alkyl, $R_4$ is a hydrogen atom or forms, with $R_2$ or $R_3$, a methylene radical or an oxo radical, $R_5$ and $R_6$ are each hydrogen or together form an oxo radical;

or a pharmaceutically acceptable salt thereof.

Illustrative embodiments of compounds of Formula I include compounds of Formula Ia, Formula Ib, and Formula Ic below:

(Ia)

(Ib)

(Ic)

In which the substituents are as defined in connection with Formula I above.

In some preferred embodiments of compounds of Formulas I, Ia, Ib, or Ic above, R is a substituent of the formula:

$$—(CH)_n—X—(CH_2)_m—Y—(C)_p—COOR'$$
$$\phantom{—(CH)_n—X—(CH_2)_m—Y—}|\phantom{—(C)_p—COO}/\phantom{R'}\backslash$$
$$\phantom{—(CH)_n—X—(CH_2)_m—Y—}R''\phantom{—(C)_p—COO}R^{\circ}\phantom{}R^{\circ\circ}$$

wherein:

R' and R" are the same or different, are hydrogen atoms or alkyl radicals,

X is a bond or represents a carbamoyl, N-methylcarbamoyl, aminocarbonyl or N-methylaminocarbonyl radical, Y is a bond or represents a phenylene radical, $R^{\circ}$ and $R^{\circ\circ}$ are the same or different, and are hydrogen atoms or alkyl radicals, or $R^{\circ}$ is hydroxyl, hydroxyalkyl, phenyl, benzyl, carbamoylmethyl or else, when Y is a bond and X is carbamoyl, $R^{\circ}$ can form a 5- or 6-membered ring with the nitrogen atom contained in X, it being possible for this ring to additionally comprise another hetero atom chosen from oxygen or sulphur and, n, m and p are each integers from 0 to 16, and m+n+p is between 4 and 16.

In some preferred embodiments of compounds of Formulas I, Ia, Ib, or Ic above, R is a substituent of the formula $$—(CH)_n—X—(CH_2)_m—Y—(C)_p—CONHZ$$
$$\phantom{—(CH)_n—X—(CH_2)_m—Y—}|\phantom{—(C)_p—CON}/\phantom{}\backslash$$
$$\phantom{—(CH)_n—X—(CH_2)_m—Y—}R''\phantom{—(C)_p—CON}R^{\circ}\phantom{}R^{\circ\circ}$$

where R", $R^{\circ}$, $R^{\circ\circ}$, X, Y, n, m and p are as given above and Z is an amino acid radical such as a standard amino acid radical joined to the adjacent carbon atom by a peptide bond to the amino terminus of the amino acid radical;

In some preferred embodiments of compounds of Formulas I, Ia, Ib, or Ic above, $R_1$ is a $C_2$ to $C_{20}$ substituted or unsubstituted carboxyacyl. Examples of suitable carboxyacyl groups include but are not limited to those shown as group $R_1$ in U.S. Pat. No. 6,172,110 to Lee et al., the disclosure of which is incorporated by reference herein in its entirety.

In some preferred embodiments of compounds of Formulas I, Ia, Ib, or Ic above, $R_{12}$ is —$CR_2R_3R_4$.

In some preferred embodiments of compounds of Formulas I, Ia, Ib, or Ic above, $R_2$ and $R_4$ together form a methylene radical.

In some preferred embodiments of compounds of Formulas I, Ia, Ib, or Ic above, $R_3$ is methyl.

In some preferred embodiments of compounds of Formulas I, Ia, Ib, or Ic above, $R_5$ and $R_6$ are each H.

In some preferred embodiments of compounds of Formulas I, Ia, Ib, or Ic above, $R_{10}$ and $R_{11}$ are each H.

In some preferred embodiments of compounds of Formulas I, Ia, Ib, or Ic above, $R_{13}$ and $R_{14}$ are each H.

An illustrative compound of the invention is a compound (compound 9 herein) having the formula:

Another illustrative compound of the invention is a compound (compound 12 herein) having the formula:

12

Another illustrative example of the present invention is a compound (compound 19 herein) having the formula:

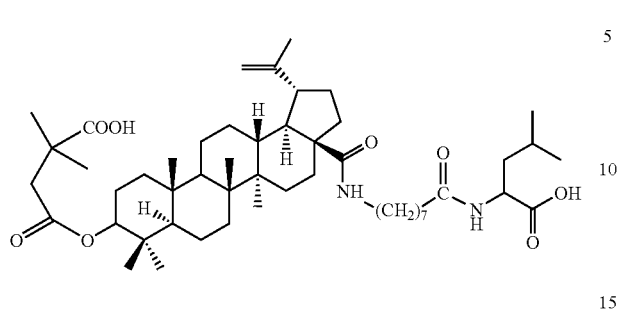

Compounds of the present invention (i.e., active compounds) can be made in accordance with Scheme I, Scheme II, and/or Scheme III below, or variations thereof that will be apparent to those skilled in the art in light of the disclosure herein.

Scheme I

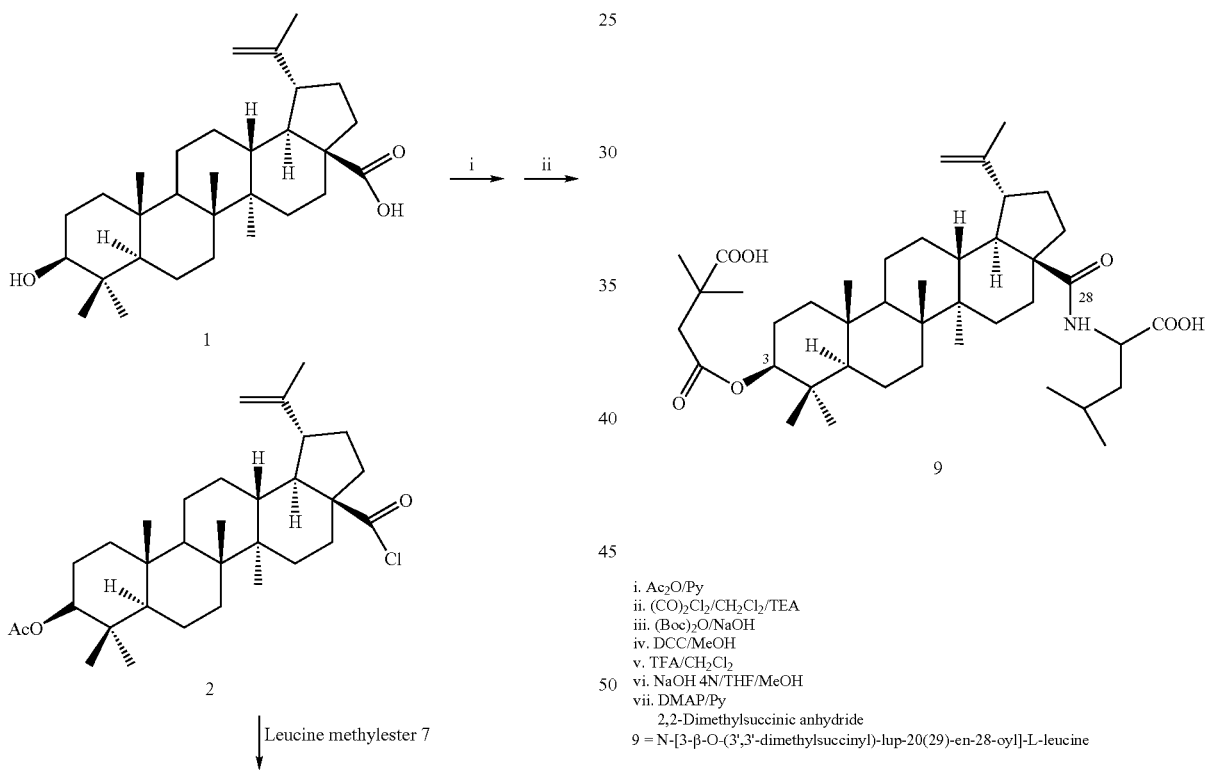

i. Ac$_2$O/Py
ii. (CO)$_2$Cl$_2$/CH$_2$Cl$_2$/TEA
iii. (Boc)$_2$O/NaOH
iv. DCC/MeOH
v. TFA/CH$_2$Cl$_2$
vi. NaOH 4N/THF/MeOH
vii. DMAP/Py
   2,2-Dimethylsuccinic anhydride
9 = N-[3-β-O-(3',3'-dimethylsuccinyl)-lup-20(29)-en-28-oyl]-L-leucine Scheme II

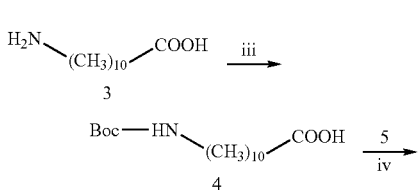

-continued
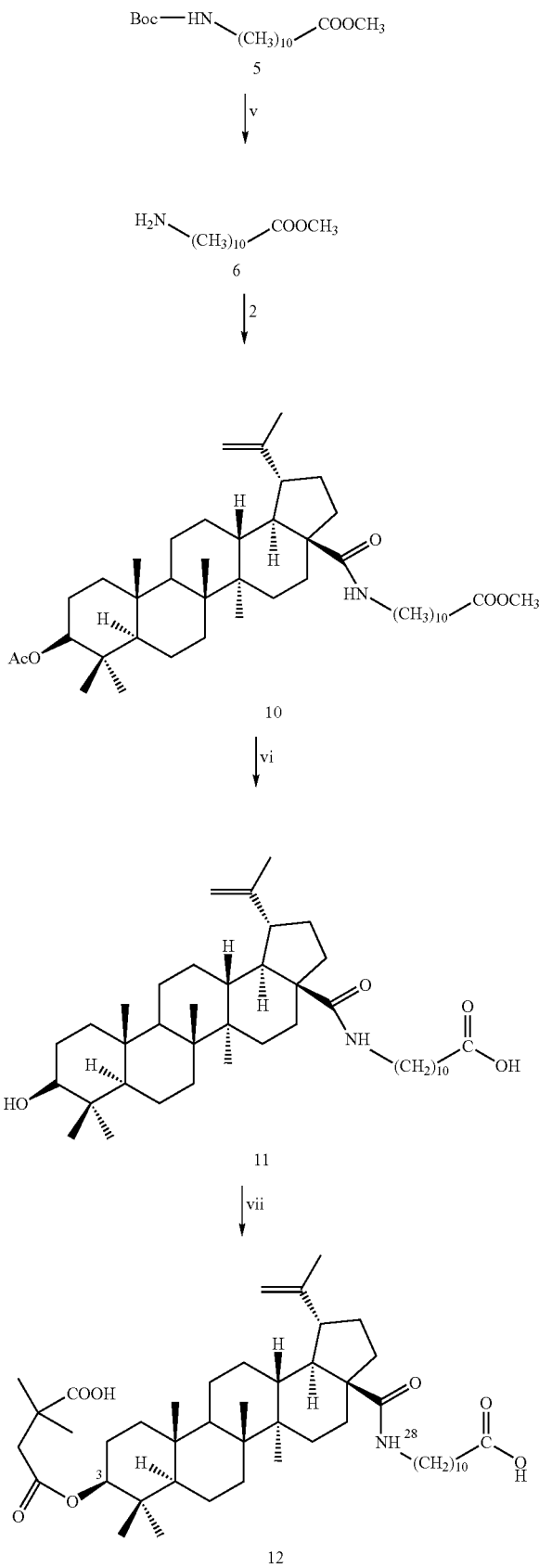

-continued
i. Ac₂O/Py
ii. (CO)₂Cl₂/CH₂Cl₂/TEA
iii. (Boc)₂O/NaOH
iv. DCC/MeOH
v. TFA/CH₂Cl₂
vi. NaOH 4N/THF/MeOH
vii. DMAP/Py
　2,2-Dimethylsuccinic anhydride
12 = N-[3-β-O-(3',3'-dimethylsuccinyl)-lup-20(29)-en-28-oyl]-11-aminoundecanoic acid
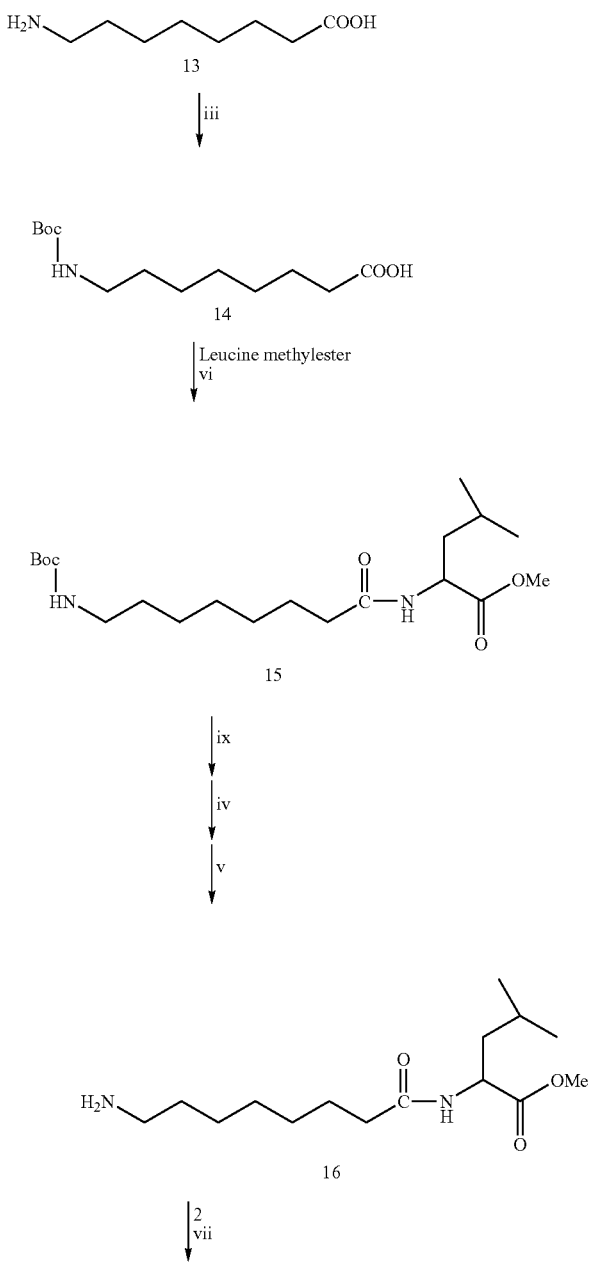
Scheme III -continued
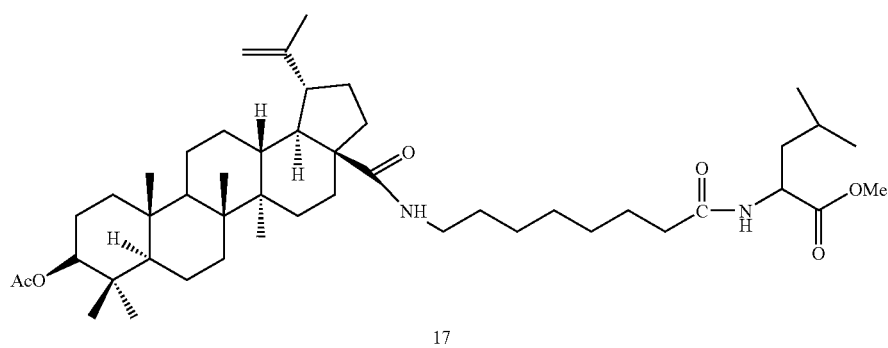
17
↓ ix
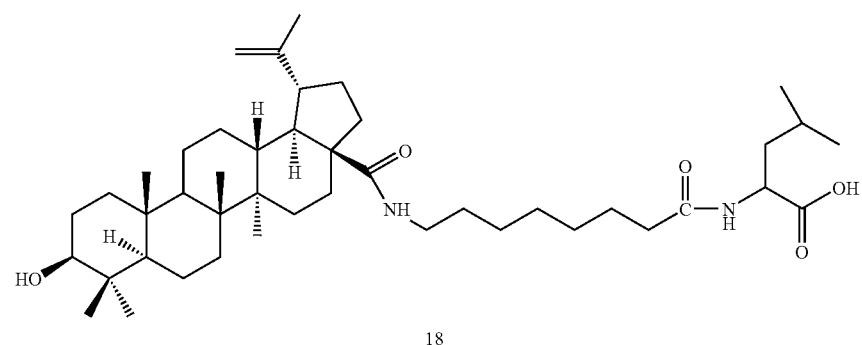
18
↓ x
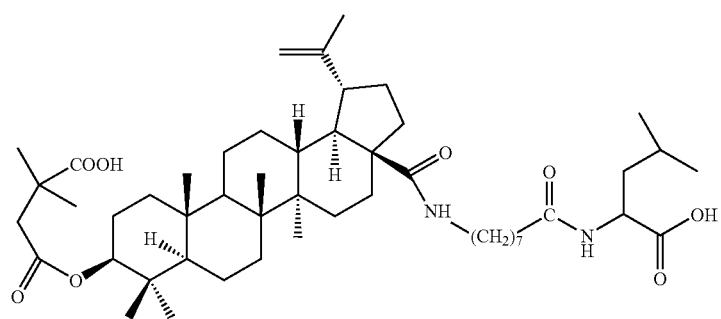
19
i. Ac$_2$O/Py
ii. SO$_2$Cl$_2$/CH$_2$Cl$_2$
iii. (Boc)$_2$O
iv. BrBz, K$_2$CO$_3$, dry Acetone, ref
v. TFA/CH$_2$Cl$_2$
vi. HOBT/EDC/Et$_3$N, 15hr
vii. Et3N/CH$_2$Cl$_2$, rt 12hr
viii. TsCl/HCl
ix. NaOH 4N/THF/MeOH
x. DMAP/Py
   2,2-Dimethylsuccinic anhydride
xi. HCl, 1N
19 = N-[N-[3-β-O-(3',3'-dimethylsuccinyl)-lup-20(29)-en-28-oyl]-8-aminooctanoyl]leucine.

Additional examples of active compounds of the present invention which may be synthesized by procedures as described above, or variations thereof which will be readily apparent to skilled persons, include compounds of the following structure:

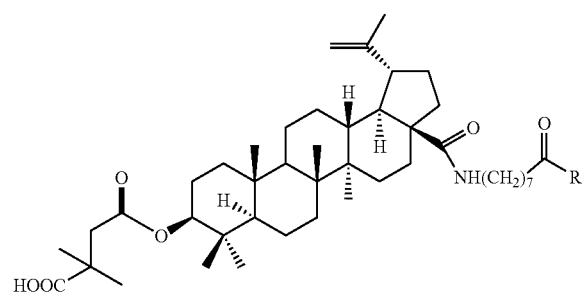

where R is L-amino acid radical such as

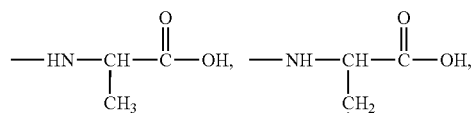
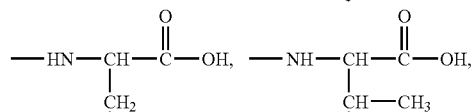
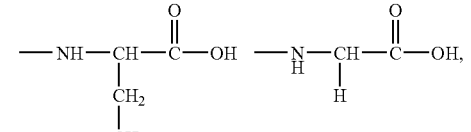
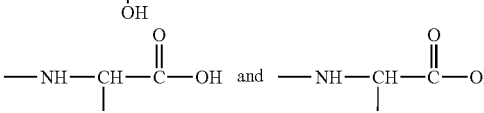

Such compounds may be named as follows:

N-[N-[3-β-O-(3',3'-dimethylsuccinyl)-lup-20(29)-en-28-oyl]-8-aminooctanoyl]alanine;

N-[N-[3-β-O-(3',3'-dimethylsuccinyl)-lup-20(29)-en-28-oyl]-8-aminooctanoyl]phenylalanine;

N-[N-[3-β-O-(3',3'-dimethylsuccinyl)-lup-20(29)-en-28-oyl]-8-aminooctanoyl]aspartate;

N-[N-[3-β-O-(3',3'-dimethylsuccinyl)-lup-20(29)-en-28-oyl]-8-aminooctanoyl]isoleucine;

N-[N-[3-β-O-(3',3'-dimethylsuccinyl)-lup-20(29)-en-28-oyl]-8-aminooctanoyl]glutamate;

N-[N-[3-β-O-(3',3'-dimethylsuccinyl)-lup-20(29)-en-28-oyl]-8-aminooctanoyl]glycine;

N-[N-[3-β-O-(3',3'-dimethylsuccinyl)-lup-20(29)-en-28-oyl]-8-aminooctanoyl]methionine; and N-[N-[3-β-O-(3',3'-dimethylsuccinyl)-lup-20(29)-en-28-oyl]-8-aminooctanoyl]valine.

Further examples of active compounds of the present invention which may be synthesized by procedures as described above, or variations thereof which will be readily apparent to skilled persons, include compounds of the following structure:

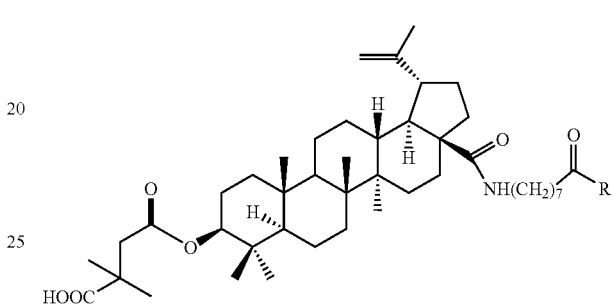

where R is a D-amino acid radical such as:

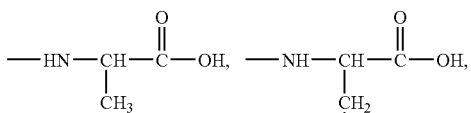
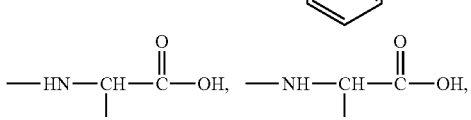
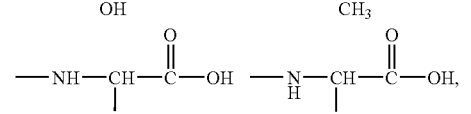
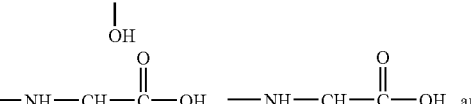
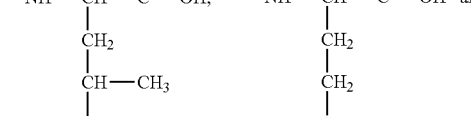

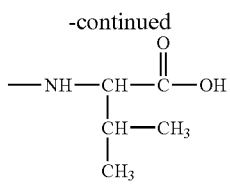

Such compounds may be named as follows:

N-[N-[3-D-O-(3',3'-dimethylsuccinyl)-lup-20(29)-en-28-oyl]-8-aminooctanoyl]-D-alanine;

N-[N-[3-β-O-(3',3'-dimethylsuccinyl)-lup-20(29)-en-28-oyl]-8-aminooctanoyl]-D-phenylalanine;

N-[N-[3-β-O-(3',3'-dimethylsuccinyl)-lup-20(29)-en-28-oyl]-8-aminooctanoyl]-D-aspartate;

N-[N-[3-β-O-(3',3'-dimethylsuccinyl)-lup-20(29)-en-28-oyl]-8-aminooctanoyl]-D-isoleucine;

N-[N-[3-β-O-(3',3'-dimethylsuccinyl)-lup-20(29)-en-28-oyl]-8-aminooctanoyl]-D-glutamate;

N-[N-[3-D-O-(3',3'-dimethylsuccinyl)-lup-20(29)-en-28-oyl]-8-aminooctanoyl]-D-glycine;

N-[N-[3-β-O-(3',3'-dimethylsuccinyl)-lup-20(29)-en-28-oyl]-8-aminooctanoyl]-D-leucine;

N-[N-[3-β-O-(3',3'-dimethylsuccinyl)-lup-20(29)-en-28-oyl]-8-aminooctanoyl]-D-methionine; and N-[N-[3-β-O-(3',3'-dimethylsuccinyl)-lup-20(29)-en-28-oyl]-8-aminooctanoyl]-D-valine.

Still further examples of active compounds of the present invention which may be synthesized by procedures as described above, or variations thereof which will be readily apparent to skilled persons, include compounds of the following structure:

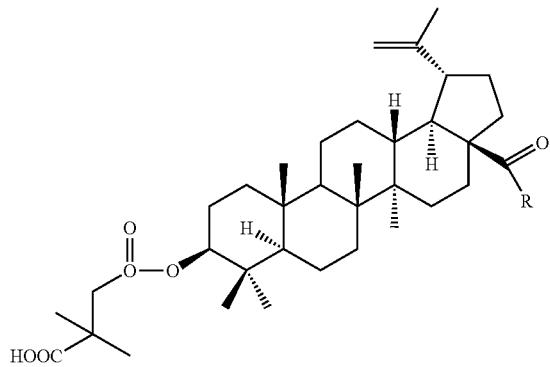

where R is a D-amino acid radical such as following:

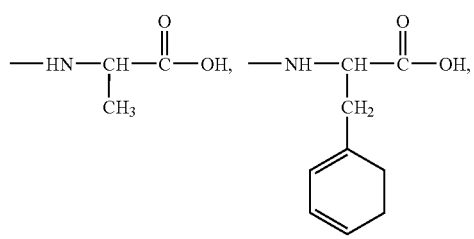

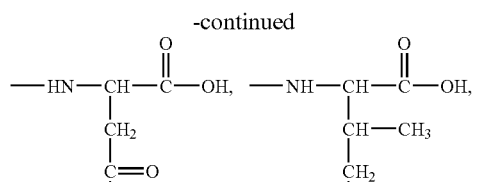

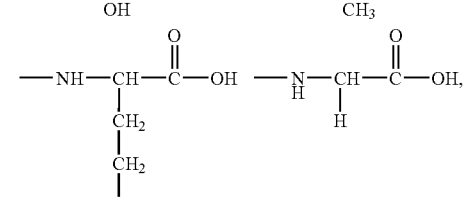

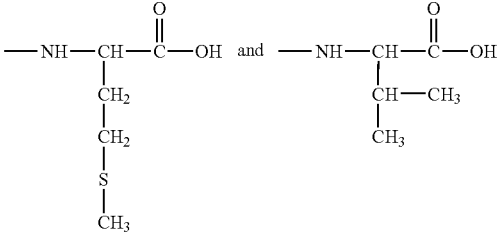

Such compounds may be named as follows:

N-[3-β-O-(3',3'-dimethylsuccinyl)-lup-20(29)-en-28-oyl]-D-alanine;

N-[3-β-O-(3',3'-dimethylsuccinyl)-lup-20(29)-en-28-oyl]-D-phenylalanine;

N-[3-β-O-(3',3'-dimethylsuccinyl)-lup-20(29)-en-28-oyl]-D-aspartate;

N-[3-β-O-(3',3'-dimethylsuccinyl)-lup-20(29)-en-28-oyl]-D-isoleucine;

N-[3-β-O-(3',3'-dimethylsuccinyl)-lup-20(29)-en-28-oyl]-D-glutamate;

N-[3-β-O-(3',3'-dimethylsuccinyl)-lup-20(29)-en-28-oyl]-D-glycine;

N-[3-β-O-(3',3'-dimethylsuccinyl)-lup-20(29)-en-28-oyl]-D-methionine; and

N-[3-β-O-(3',3'-dimethylsuccinyl)-lup-20(29)-en-28-oyl]-D-valine.

Still further examples of active compounds of the present invention which may be synthesized by procedures as described above, or variations thereof which will be readily apparent to skilled persons, include compounds of the following structure:

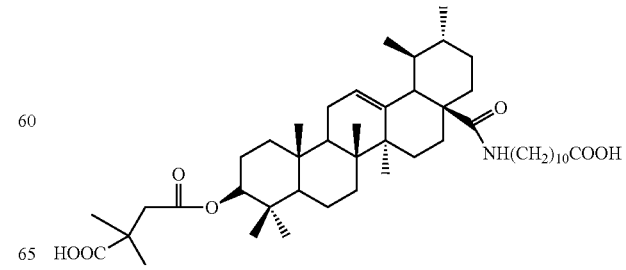

or N-[3-β-O-(3',3'-dimethylsuccinyl)-olean-12-en-28-oyl]-11-aminoundecanoic acid;

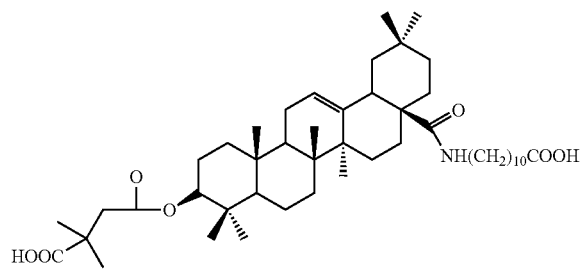

or N-[3-β-O-(3',3'-dimethylsuccinyl)-urs-12-en-28-oyl]-11-aminoundecanoic acid;

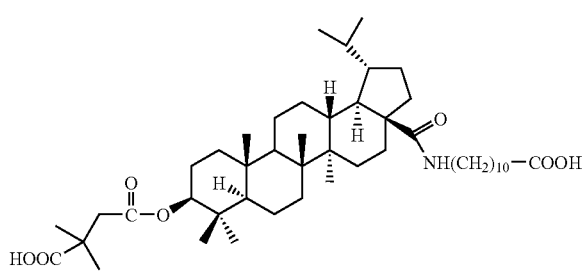

or N-[3-β-O-(3',3'-dimethylsuccinyl)-lupane-28-oyl]-11-aminoundecanoic acid.

Still further examples of active compounds of the present invention which may be synthesized by procedures as described above, or variations thereof which will be readily apparent to skilled persons, include the following:

N-[N-[3-β-O-(3',3'-dimethylsuccinyl)-lup-20(29)-en-28-oyl]-11-aminoundecanoyl]alanine;
N-[N-[3-β-O-(3',3'-dimethylsuccinyl)-lup-20(29)-en-28-oyl]-11-aminoundecanoyl]phenylalanine;
N-[N-[3-β-O-(3',3'-dimethylsuccinyl)-lup-20(29)-en-28-oyl]-11-aminoundecanoyl]aspartate;
N-[N-[3-β-O-(3',3'-dimethylsuccinyl)-lup-20(29)-en-28-oyl]-11-aminoundecanoyl]isoleucine;
N-[N-[3-β-O-(3',3'-dimethylsuccinyl)-lup-20(29)-en-28-oyl]-11-aminoundecanoyl]glutamate;
N-[N-[3-β-O-(3',3'-dimethylsuccinyl)-lup-20(29)-en-28-oyl]-11-aminoundecanoyl]glycine;
N-[N-[3-β-O-(3',3'-dimethylsuccinyl)-lup-20(29)-en-28-oyl]-11-aminoundecanoyl]leucine;
N-[N-[3-β-O-(3',3'-dimethylsuccinyl)-lup-20(29)-en-28-oyl]-11-aminoundecanoyl]methionine;
N-[N-[3-β-O-(3',3'-dimethylsuccinyl)-lup-20(29)-en-28-oyl]-11-aminoundecanoyl]valine;
N-[N-[3-β-O-(3',3'-dimethylsuccinyl)-olean-12-en-28-oyl]-11-aminoundecanoyl]alanine;
N-[N-[3-β-O-(3',3'-dimethylsuccinyl)-olean-12-en-28-oyl]-11-aminoundecanoyl]phenylalanine;
N-[N-[3-β-O-(3',3'-dimethylsuccinyl)-olean-12-en-28-oyl]-11-aminoundecanoyl]aspartate;
N-[N-[3-β-O-(3',3'-dimethylsuccinyl)-olean-12-en-28-oyl]-11-aminoundecanoyl]isoleucine;
N-[N-[3-β-O-(3',3'-dimethylsuccinyl)-olean-12-en-28-oyl]-11-aminoundecanoyl]glutamate;
N-[N-[3-β-O-(3',3'-dimethylsuccinyl)-olean-12-en-28-oyl]-11-aminoundecanoyl]glycine;
N-[N-[3-β-O-(3',3'-dimethylsuccinyl)-olean-12-en-28-oyl]-11-aminoundecanoyl]leucine;
N-[N-[3-β-O-(3',3'-dimethylsuccinyl)-olean-12-en-28-oyl]-11-aminoundecanoyl]methionine;
N-[N-[3-β-O-(3',3'-dimethylsuccinyl)-olean-12-en-28-oyl]-11-aminoundecanoyl]valine;
N-[N-[3-β-O-(3',3'-dimethylsuccinyl)-olean-12-en-28-oyl]-8-aminooctanoyl]alanine;
N-[N-[3-β-O-(3',3'-dimethylsuccinyl)-olean-12-en-28-oyl]-8-aminooctanoyl]phenylalanine;
N-[N-[3-β-O-(3',3'-dimethylsuccinyl)-olean-12-en-28-oyl]-8-aminooctanoyl]aspartate;
N-[N-[3-β-O-(3',3'-dimethylsuccinyl)-olean-12-en-28-oyl]-8-aminooctanoyl]isoleucine;
N-[N-[3-β-O-(3',3'-dimethylsuccinyl)-olean-12-en-28-oyl]-8-aminooctanoyl]glutamate;
N-[N-[3-β-O-(3',3'-dimethylsuccinyl)-olean-12-en-28-oyl]-8-aminooctanoyl]glycine;
N-[N-[3-β-O-(3',3'-dimethylsuccinyl)-olean-12-en-28-oyl]-8-aminooctanoyl]leucine;
N-[N-[3-β-O-(3',3'-dimethylsuccinyl)-olean-12-en-28-oyl]-8-aminooctanoyl]methionine;
N-[N-[3-β-O-(3',3'-dimethylsuccinyl)-olean-12-en-28-oyl]-8-aminooctanoyl]valine;
N-[N-[3-β-O-(3',3'-dimethylsuccinyl)-urs-12-en-28-oyl]-11-aminoundecanoyl]alanine;
N-[N-[3-β-O-(3',3'-dimethylsuccinyl)-urs-12-en-28-oyl]-11-aminoundecanoyl]phenylalanine;
N-[N-[3-β-O-(3',3'-dimethylsuccinyl)-urs-12-en-28-oyl]-11-aminoundecanoyl]aspartate;
N-[N-[3-β-O-(3',3'-dimethylsuccinyl)-urs-12-en-28-oyl]-11-aminoundecanoyl]isoleucine;
N-[N-[3-β-O-(3',3'-dimethylsuccinyl)-urs-12-en-28-oyl]-11-aminoundecanoyl]glutamate;
N-[N-[3-β-O-(3',3'-dimethylsuccinyl)-urs-12-en-28-oyl]-11-aminoundecanoyl]glycine;
N-[N-[3-β-O-(3',3'-dimethylsuccinyl)-urs-12-en-28-oyl]-11-aminoundecanoyl]leucine;
N-[N-[3-β-O-(3',3'-dimethylsuccinyl)-urs-12-en-28-oyl]-11-aminoundecanoyl]methionine;
N-[N-[3-β-O-(3',3'-dimethylsuccinyl)-urs-12-en-28-oyl]-11-aminoundecanoyl]valine;
N-[N-[3-β-O-(3',3'-dimethylsuccinyl)-urs-12-en-28-oyl]-8-aminooctanoyl]alanine;
N-[N-[3-β-O-(3',3'-dimethylsuccinyl)-urs-12-en-28-oyl]-8-aminooctanoyl]phenylalanine;
N-[N-[3-β-O-(3',3'-dimethylsuccinyl)-urs-12-en-28-oyl]-8-aminooctanoyl]aspartate;
N-[N-[3-β-O-(3',3'-dimethylsuccinyl)-urs-12-en-28-oyl]-8-aminooctanoyl]isoleucine;
N-[N-[3-β-O-(3',3'-dimethylsuccinyl)-urs-12-en-28-oyl]-8-aminooctanoyl]glutamate;
N-[N-[3-β-O-(3',3'-dimethylsuccinyl)-urs-12-en-28-oyl]-8-aminooctanoyl]glycine;
N-[N-[3-β-O-(3',3'-dimethylsuccinyl)-urs-12-en-28-oyl]-8-aminooctanoyl]leucine;
N-[N-[3-β-O-(3',3'-dimethylsuccinyl)-urs-12-en-28-oyl]-8-aminooctanoyl]methionine;
N-[N-[3-β-O-(3',3'-dimethylsuccinyl)-urs-12-en-28-oyl]-8-aminooctanoyl]valine;
N-[N-[3-β-O-(3',3'-dimethylsuccinyl)-lupane-28-oyl]-11-undecanoyl]alanine;
N-[N-[3-β-O-(3',3'-dimethylsuccinyl)-lupane-28-oyl]-11-undecanoyl]phenylalanine;

N-[N-[3-β-O-(3',3'-dimethylsuccinyl)-lupane-28-oyl]-11-undecanoyl]aspartate;

N-[N-[3-β-O-(3',3'-dimethylsuccinyl)-lupane-28-oyl]-11-undecanoyl]isoleucine;

N-[N-[3-β-O-(3',3'-dimethylsuccinyl)-lupane-28-oyl]-11-undecanoyl]glutamate;

N-[N-[3-β-O-(3',3'-dimethylsuccinyl)-lupane-28-oyl]-11-undecanoyl]glycine;

N-[N-[3-β-O-(3',3'-dimethylsuccinyl)-lupane-28-oyl]-11-undecanoyl]leucine;

N-[N-[3-β-O-(3',3'-dimethylsuccinyl)-lupane-28-oyl]-11-undecanoyl]methionine;

N-[N-[3-β-O-(3',3'-dimethylsuccinyl)-lupane-28-oyl]-11-undecanoyl]valine;

N-[N-[3-β-O-(3',3'-dimethylsuccinyl)-lupane-28-oyl]-8-aminooctanoyl]alanine;

N-[N-[3-β-O-(3',3'-dimethylsuccinyl)-lupane-28-oyl]-8-aminooctanoyl]phenylalanine;

N-[N-[3-β-O-(3',3'-dimethylsuccinyl)-lupane-28-oyl]-8-aminooctanoyl]aspartate;

N-[N-[3-β-O-(3',3'-dimethylsuccinyl)-lupane-28-oyl]-8-aminooctanoyl]isoleucine;

N-[N-[3-β-O-(3',3'-dimethylsuccinyl)-lupane-28-oyl]-8-aminooctanoyl]glutamate;

N-[N-[3-β-O-(3',3'-dimethylsuccinyl)-lupane-28-oyl]-8-aminooctanoyl]glycine;

N-[N-[3-β-O-(3',3'-dimethylsuccinyl)-lupane-28-oyl]-8-aminooctanoyl]leucine;

N-[N-[3-β-O-(3',3'-dimethylsuccinyl)-lupane-28-oyl]-8-aminooctanoyl]methionine; and N-[N-[3-β-O-(3',3'-dimethylsuccinyl)-lupane-28-oyl]-8-aminooctanoyl]valine.

The active compounds disclosed herein or described above can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

2. Pharmaceutical Formulations.

The active compounds described above may be formulated for administration in a pharmaceutical carrier in accordance with known techniques. See, e.g., Remington, *The Science And Practice of Pharmacy* (9th Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unitdose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 1 or 10 mg to about 100 milligrams, 1 gram or 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

In addition to compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Methods of Treatment.

The present invention is primarily concerned with the treatment of human subjects, but the invention may also be carried out on animal subjects, particularly mammalian subjects such as mice, rats, dogs, cats, non-human primates, livestock and horses for veterinary purposes, and for drug screening and drug development purposes.

Examples of retroviral infections that may be treated by the methods of the present invention include but are not limited to feline leukemia virus (FeLV), human immunodeficiency virus (HIV; including both HIV-1 and HIV-2) simian immunodeficiency virus (SIV) and other lentiviral infections such as equine infectious anemia virus (EAIV) and feline immunodeficiency virus (FIV). A particularly preferred embodiment is use of the methods, compounds and compositions of the present invention for the treatment of HIV-1 infection in human subjects.

In one embodiment of the present invention, the methods may be used to treat HIV-1 infections that are resistant to treatment with DSB or a pharmaceutically acceptable salt thereof and/or resistant to treatment with RPR103611 or a pharmaceutically acceptable salt thereof (these two compounds illustrated below).

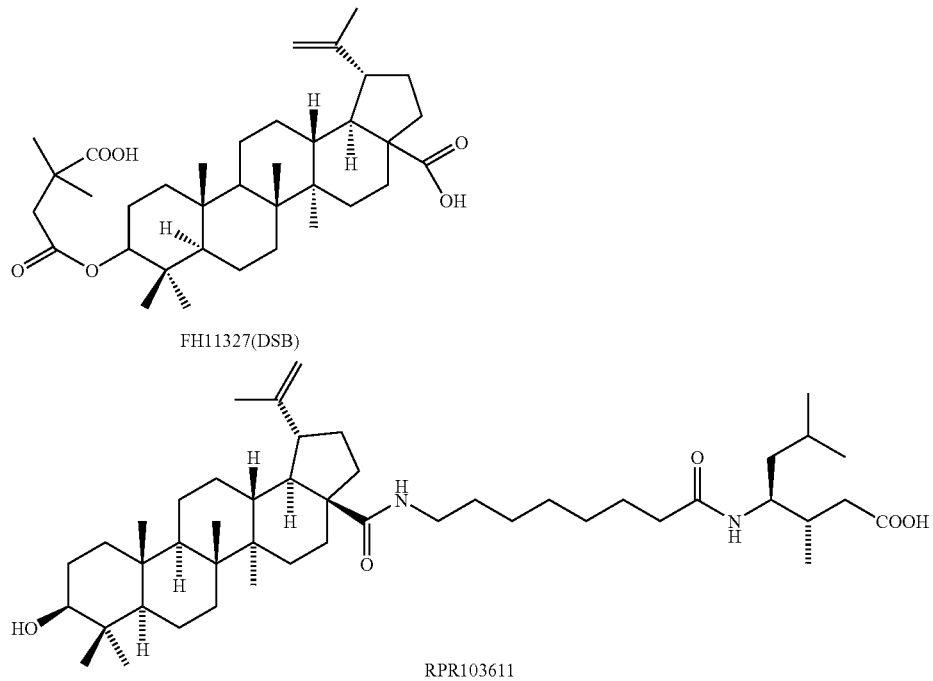

By "resistant" is meant that the efficacy of the compound to which resistance has developed is significantly reduced as compared to infections which are not resistant to treatment with the same compound or compounds.

Without wishing to be bound to any particular theory of the instant invention, it is believed (and preferred) that compounds of the present invention interfere with two different and distinct steps of the HIV-1 life cycle: first, compounds of the present invention inhibit the early step of HIV-1 entry into cells; second, compounds of the present invention inhibit HIV-1 maturation within cells (e.g., by inhibiting the last step of HIV-1 gag processing, the cleavage between P24 and p2 required for HIV-1 maturation). The pharmacophore believed responsible for the anti-entry activity is believed to reside at the 3 position and the side chain substituted thereon, and the pharmacophore believed responsible for the anti-maturation activity is believed to reside at the 28 position and side-chain substituted thereon 4. Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any one active agent, the use of which is in the scope of present invention, will vary somewhat from compound to compound, and patient to patient, and will depend upon factors such as the age and condition of the patient and the route of delivery. Such dosages can be determined in accordance with routine pharmacological procedures known to those skilled in the art. Typical dosages comprise at about 0.1 to about 100 mg/kg body weight. One preferred dosages comprise about 1 to about 100 mg/kg body weight of the active ingredient. One still more preferred dosages comprise about 10 to about 100 mg/kg body weight.

5. Combination Methods and Compositions.

Methods of treatment as described herein can include concurrently administering one or more additional anti-viral agent, and compositions as described herein can optionally include one or more additional antiviral agents. Examples of such additional antiviral agents include, but are not limited to, AZT (Glaxo Wellcome), 3TC (Glaxo Wellcome), ddI (Bristol-Myers Squibb), ddC (Hoffmann-La Roche), D4T (Bristol-Myers Squibb), abacavir (Glaxo Wellcome), nevirapine (Boehringher Ingelheim), delavirdine (Pharmacia and Upjohn), efavirenz (DuPont Pharmaceuticals), saquinavir (Hoffmann-La Roche), ritonavir (Abbott Laboratories), indinavir (Merck and Company), nelfinavir (Agouron Pharmaceuticals), amprenavir (Glaxo Wellcome), adefovir (Gilead Sciences), hydroxyurea (Bristol-Meyers Squibb), AL-721 (lipid mixture) manufactured by Ethigen Corporation and Matrix Research Laboratories; Amphotericin B methyl ester; Ampligen (mismatched RNA) developed by DuPont/ HEM Research; anti-AIDS antibody (Nisshon Food); 1 AS-101 (heavy metal based immunostimulant); Betaseron (.beta.-interferon) manufactured by Triton Biosciences (Shell Oil); butylated hydroxytoluene; Carrosyn (polymannoacetate); Castanospermine; Contracan (stearic acid derivative); Creme Pharmatex (containing benzalkonium chloride) manufactured by Pharmalec; CS-87 (5-unsubstituted derivative of Zidovudine), Cytovene (ganciclovir) manufactured by Syntex Corporation; dextran sulfate; D-penicillamine (3-mercapto-D-valine) manufactured by Carter-Wallace and Degussa Pharmaceutical; Foscarnet (trisodium phosphonoformate) manufactured by Astra AB; fusidic acid manufactured by Leo Lovens; glycyrrhizin (a constituent of licorice root); HPA-23 (ammonium-21-tungsto-9-antimonate) manufactured by Rhone-Poulenc Sante; human immune virus antiviral developed by Porton Products International; Ornidyl (eflornithine) manufactured by Merrell-Dow; nonoxinol; pentamidine isethionate (PEN-TAM-300) manufactured by Lypho Med; Peptide T (octapeptide sequence) manufactured by Peninsula Laboratories; Phenyloin (Warner-Lambert); Ribavirin; Rifabutin (ansamycin) manufactured by Adria Laboratories; CD4-IgG2 (Progenics Pharmaceuticals) or other CD4-containing or CD4-based molecules; T-20(Trimeris); Trimetrexate manufactured by Warner-Lambert Company; SK-818 (germanium-derived antiviral) manufactured by Sanwa Kagaku; suramin and analogues thereof manufactured by Miles Pharmaceuticals; UA001 manufactured by Ueno Fine Chemicals Industry; and alpha-interferon, manufactured by Glaxo Wellcome.

Pharmaceutical compositions of the present invention can also further comprise immunomodulators, and methods of treatment of the present invention can include the co-administration of an immunomodulator. Suitable immunomodulators for optional use with the active compounds of the present invention in accordance with the present invention can include, but are not limited to: ABPP (Bropririmine); Ampligen (mismatched RNA) DuPont M Research; anti-human interferon-.alpha.-antibody (Advance Biotherapy and Concepts); anti-AIDS antibody (Nisshon Food); AS-101 (heavy metal based immunostimulant; ascorbic acid and derivatives thereof; interferon-.beta.; Carrosyn (polymannoacetate); Ciamexon (Boehringer-Mannheim); cyclosporin; cimetidine; CL-246,738 (American Cyanamid); colony stimulating factors, including GM-CSF (Sandoz, Genetics Institute); dinitrochlorobenzene; HE2000 (Hollis-Eden Pharmaceuticals); interferon-.alpha.; inteferon-gamma; glucan; hyperimmune gamma-globulin (Bayer); IMREG-1 (leukocyte dialyzate) and IMREG-2 (IMAREG Corp.); immuthiol (sodium diethylthiocarbamate) (Institut Merieux); interleukin-1 (Cetus Corporation; Hoffmann-LaRoche; Immunex); interleukin-2 (IL-2) (Chiron Corporation); isoprinosine (inosine pranobex); Krestin (Sankyo); LC-9018 (Yakult); lentinan (Ajinomoto/Yamanouchi); LF-1695 (Fournier); methionine-enkephalin (TNI Pharmaceuticals; Sigma Chemicals); Minophagen C; muramyl tripeptide, MTP-PE (Ciba-Geigy); naltrexone ("Trexan" DuPont); Neutropin, RNA immunomodulator (Nippon Shingaku); Remune (Immune Response Corporation); Reticulose (Advanced Viral Research Corporation); shosaikoto and ginseng; thymic humoral factor; TP-05 (Thymopentin, Ortho Pharmaceuticals); Thymosin factor 5 and Thymosin 1; Thymostimulin; TNF (Tumor necrosis factor) manufactured by Genentech; and vitamin B preparations.

The present invention is explained in greater detail in the following non-limiting Examples.

EXAMPLE 1

Synthesis of N-[3-O-(3',3'-dimethylsuccinyl)-lup-20 (29)-ene-28-oyl]leucine (compound 9)

The procedure to prepare 3-acyl betulinic acid (BA) is known. Briefly, the starting material betulinic acid (1) in anhydrous pyridine was added with acetic anhydride and DMAP, and refluxed for 4 hrs. The reaction mixture was cooled, then extracted with organic solvent and washed with water. The organic layer was concentrated and chromatographed on Si-gel to give 3-O-acetate BA as a white powder with a yield of 60%.

3-O-acetate BA was then dissolved in 2M $(CO)_2Cl_2$ and stirred for 1 hr. The reaction mixture was concentrated to dryness using $N_2$. The resulting acid chloride (2) was used without purification (see Scheme I above).

The acid chloride (5) in dry DCM was added to the leucine methyl ester and was then added in a triethylamine solution. After stirring for 8 hrs, the reaction was concentrated as described above and chromatographed on Si-gel to yield white powder 8 (72% yield). $^1$H NMR with signal assignment was performed to verify the structure of compound 8.

The intermediate compound 8 was dissolved in 50% methanol/THF and mixed in 4N NaOH (a quarter volume of reaction mixture). After stirring overnight, the reaction mixture was acidified with 1N HCl. The resulting precipitate was collected by filtration and washed with water. The product was dried under reduced pressure at 40° C. (92% yield). $^1$H NMR with signal assignment was performed to verify its structure.

The above product in anhydrous pyridine was added with DMAP and 10 eq. of 2,2-dimethylsuccinic anhydride. The reaction mixture was refluxed for 5 hours and acidified with 1 N HCl, diluted with $CH_2Cl_2$. The organic layer was washed with water and concentrated under vacuum. The resulted gum was purified with HPLC to yield compound 9 as white powder (65%).

EXAMPLE 2

Synthesis of N-[3-O-(3',3'-dimethylsuccinyl)-lup-20 (29)-ene-28-oyl]-11-aminoundecanoic acid (compound 12)

The Boc protected aminoundecanoic acid methyl ester (5) was obtained with a two-step synthesis: 1). di-tert-butyl dicarbonate and NaOH was added to the aqueous solution (dioxane/water) of aminoundecanoic acid. The reaction was performed overnight and the product was extracted with EtOAc. 2). The Boc-aminoundecanoic acid was subsequently subjected to methylation with MeOH catalyzed with DCC. The resulted compound 5 was obtained after chromatographed on Si-gel. The Boc group was removed with 55% TFA/DCM at room temperature for 45 min. The crude product 6 was used for the next step without purification. The coupling of compound 6 with acid chloride species yielded compound 10 under the same reaction conditions described above for compound 8. Compound 10 was subsequently subjected to the same reactions as described for compound 8 and yielded the final compound 12 (see Scheme II above).

EXAMPLE 2

Biological Activity

FIG. 1 graphically illustrates the anti-HW activity of Compound 12 (also called compound LH 55-1). In FIG. 1, PI-R represents a multiple HIV-1 protease inhibitor resistant strain of HIV-1. RT-R represents a multiple HIV-1 reverse transcriptase inhibitor resistant strain of HIV-1; NL4-3 represents a T-cell line adapted HIV-1 strain; and NL4-3/AZT represents the effect of AZT on the NL4-3virus. Note the substantial antiviral activity of compound 12 against all resistant strains.

Figure 2:
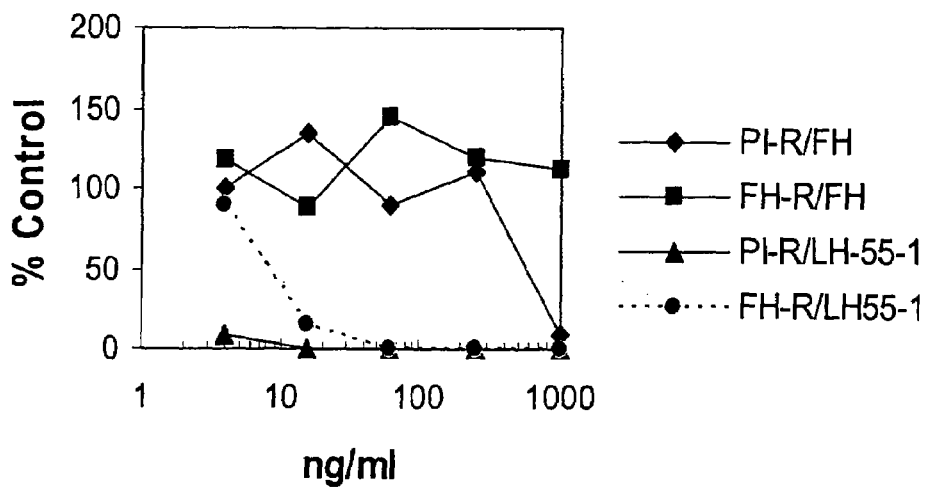
FIG. 2: The multiple protease inhibitor resistant viruses and the DSB resistant virus are resistant to DSB but are very sensitive to LH55-1. (PI-R: A multiple HIV-1 protease inhibitor resistant strain. FH-R: DSB resistant HIV-1 strain. FH=DSB).

FIG. 2 graphically illustrates that multiple protease inhibitor resistant strains of HIV-1 and DSB resistant HIV-1 are sensitive to Compound 12 (LH55-1). PI-R indicates a multiple HIV-1 protease inhibitor resistant strain of HIV-1, and FH-R indicates a DSB resistant HIV-1 strain (FH=DSB).

EXAMPLE 3

Inhibition of Membrane Fusion

Figure 3:
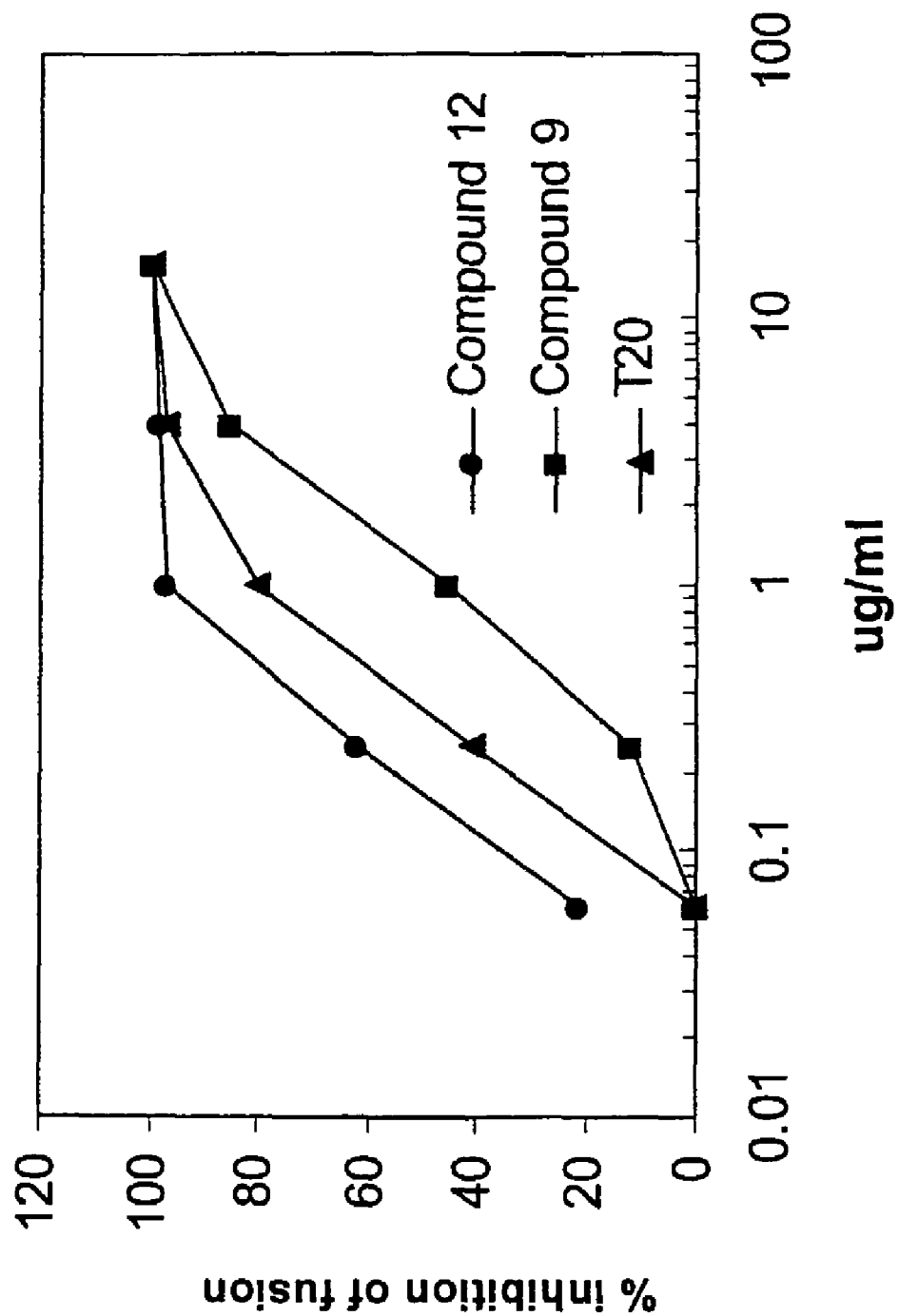
FIG. 3. LH55-1 (compound 12) and compound 9 inhibit HIV-1 entry. Fusion between COS cells expressing NL4-3 envelope glycoproteins and Hela cells expressing CD4 and CXCR4 were performed in the presence of compound 9, 12 and T20 as indicated in the figure.

To determine the mechanisms of action, the ability of LH55-1 and compound 9 to inhibit HIV-1 entry were analyzed by using a cell-cell fusion assay. Inhibition of HIV-1 envelope-mediated membrane fusion will prevent HIV-1 from entering into the cells. FIG. 3 shows that LH55-1 is a potent HIV-1 entry inhibitor that can block HIV-1 envelope-mediated membrane fusion at sub-micromolar concentrations. Compound 9 also exhibited anti-HIV-1 entry activity, albeit at higher concentrations than compound 12. T20is a polypeptide fusion inhibitor recently approved for anti-HIV-1 therapy by FDA, USA.

EXAMPLE 4

Inhibition of Viral Maturation

P24 is the capsid protein of HIV-1 and is essential for viral infectivity. P25 is the precursor of p24. Inhibition of the processing of P25 into p24 will result in an immature viral particle without infectivity. The accumulation of P25 in the presence of LH55-1 (FIG. 4, lane B) suggests that maturation of HIV-1 virions were blocked by the compound. Further studies in our laboratory indicate that the amino acids at the C-terminus of P24 are critical determinant for the drug sensitivity. The anti-HIV-1 maturation activity of LH55-1 is different from that of HIV-1 protease inhibitors since maturation of other HIV-1 gag proteins such as P17 in not affected by LH55-1.

The foregoing is illustrative of the present invention, and is not to be construed as limiting thereof. The invention is defined by the following claims, with equivalents of the claims to be included therein.

What is claimed is:
1. A compound according to Formula I:

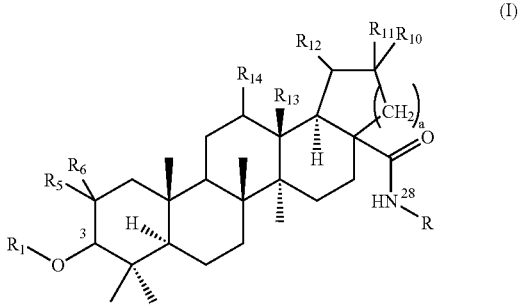

wherein:
a is 1 or 2;
$R_{10}$ and $R_{11}$ are each either H or loweralkyl;
$R_{12}$ is H, loweralkyl, or —$CR_2R_3R_4$;
$R_{13}$ and $R_{14}$ are each either H or form a bond with one another;
R is a substituent of the formula:

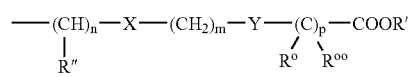

wherein:
R' and R" are the same or different, are hydrogen atoms or alkyl radicals,
X is a bond or represents a carbamoyl, N-methylcarbamoyl, aminocarbonyl or N-methylaminocarbonyl radical,
Y is a bond or represents a phenylene radical,
$R^{\circ}$ and $R^{\circ\circ}$ are the same or different, and are hydrogen atoms or alkyl radicals, or $R^{\circ}$ is hydroxyalkyl, phenyl, benzyl, carbamoylmethyl or else, when Y is a bond and X is carbamoyl, $R^{\circ}$ can form a 5- or 6-membered ring with the nitrogen atom contained in X, it being possible for this ring to additionally comprise another hetero atom chosen from oxygen or sulphur and,
n, m and p are each integers from 0 to 16, and m+n+p is between 4 and 16; or
R is a substituent of the formula $$-(CH)_n-X-(CH_2)_m-Y-(C)_p-CONHZ$$
$$\underset{R''}{|} \quad \underset{R^{\circ} \ R^{\circ\circ}}{/\ \backslash}$$

where R", $R^{\circ}$, $R^{\circ\circ}$, X, Y, n, m and p are as given above and Z is an amino acid radical joined to the adjacent nitrogen atom by a peptide bond to the amino terminus of the amino acid radical;
$R_1$ is a $C_2$ to $C_{20}$ substituted or unsubstituted carboxyacyl; or
$R_1$ is a substituent of the formula

[chemical structures shown]

where $R_a$ and $R_b$ are the same or different and are each either hydrogen or loweralkyl, and i is an integer of from 0 to 3;
$R_2$ is a methyl radical or forms with $R_4$ a methylene radical or an oxo radical,
$R_3$ is a hydroxyl, methyl or hydroxymethyl radical or a radical $-CH_2 OR'_2$, $-CH_2SR'_2$ or $-CH_2NHR'_2$ for which $R'_2$ is alkyl, hydroxyalkyl, dihydroxyalkyl, acetamidoalkyl or acetyl, or $R_2'$ is an amino radical substituted with a hydroxyalkyl or carboxyhydroxyalkyl radical, or a dialkylamino radical, the alkyl parts of which can form, with the nitrogen atom to which they are joined, a 5- or 6-membered heterocycle optionally containing another hetero atom chosen from oxygen, sulphur or nitrogen and, optionally, N-alkyl,
$R_4$ is a hydrogen atom or forms, with $R_2$ or $R_3$, a methylene radical or an oxo radical,
$R_5$ and $R_6$ are each hydrogen or together form an oxo radical; or a pharmaceutically acceptable salt thereof; subject to the proviso that:
When a=2, $R_{11}$ and $R_{10}$ are methyl, $R_{13}$ and $R_{14}$ form a double bond, R' is an alkyl radical;

and subject to the proviso that:
(i) $R_{12}$ is $-CR_2R_3R_4$; or
(ii) $R_2$ and $R_4$ together form a methylene radical; or
(iii) $R_3$ is methyl; or
(iv) $R_{10}$ and $R_{11}$ are each H; or
(v) $R_{13}$ and $R_{14}$ are each H.

2. A compound of claim 1, wherein R is a substituent of the formula:

$$-(CH)_n-X-(CH_2)_m-Y-(C)_p-COOR'$$
$$\underset{R''}{|} \quad \underset{R^{\circ} \ R^{\circ\circ}}{/\ \backslash}$$

wherein:
R' and R" are the same or different, are hydrogen atoms or alkyl radicals,
X is a bond or represents a carbamoyl, N-methylcarbamoyl, aminocarbonyl or N-methylaminocarbonyl radical,
Y is a bond or represents a phenylene radical,
$R^{\circ}$ and $R^{\circ\circ}$ are the same or different, and are hydrogen atoms or alkyl radicals (it being understood that $R^{\circ}$ and $R^{\circ\circ}$ are not necessarily identical on each unit $-CR^{\circ}R^{\circ\circ}-$), or $R^{\circ}$ is hydroxyl, hydroxyalkyl, phenyl, benzyl, carbamoylmethyl or else, when Y is a bond and X is carbamoyl, $R^{\circ}$ can form a 5- or 6-membered ring with the nitrogen atom contained in X, it being possible for this ring to additionally comprise another hetero atom chosen from oxygen or sulphur and,
n, m and p are each integers from 0 to 16, and m+n+p is between 4 and 16.

3. A compound of claim 1, wherein $R_1$ is a $C_2$ to $C_{20}$ substituted or unsubstituted carboxyacyl.

4. A compound of claim 1, wherein $R_{12}$ is $-CR_2R_3R_4$.

5. The compound of claim 1, wherein $R_5$ and $R_6$ are each H.

6. The compound of claim 1, wherein $R_2$ and $R_4$ together form a methylene radical.

7. The compound of claim 1, wherein $R_3$ is methyl.

8. The compound of claim 1, wherein $R_{10}$ and $R_{11}$ are each H.

9. The compound of claim 1, wherein $R_{13}$ and $R_{14}$ are each H.

10. A composition comprising a compound of claim 1 in a pharmaceutically acceptable carrier.

11. The composition according to claim 10, wherein said carrier comprises an aqueous solution.

12. A method of treating a retroviral infection in a subject in need thereof, comprising administering to said subject a compound of claim 1 in an amount effective to treat said retroviral infection.

13. The method of claim 12, wherein said retroviral infection is an HIV-1 infection.

14. The method of claim 13, wherein said HIV-1 infection is a DSB-resistant HIV-1 infection.

15. The method of claim 13, wherein said HIV-1 infection is an RPR103611-resistant HIV-1 infection.

* * * * *